United States Patent [19]

Schneider

[11] 4,197,465
[45] Apr. 8, 1980

[54] X-RAY TABLE

[75] Inventor: Edward T. Schneider, Willoughby Hills, Ohio

[73] Assignee: Picker Corporation, Cleveland, Ohio

[21] Appl. No.: 857,217

[22] Filed: Nov. 29, 1977

[51] Int. Cl.² ............... G01N 21/00; G01N 23/00
[52] U.S. Cl. ........................... 250/439 R; 250/456
[58] Field of Search ............ 250/439, 444, 445 R, 250/445 T, 446, 447, 448, 449, 450, 451, 456; 269/322, 323

[56] References Cited
U.S. PATENT DOCUMENTS

| 3,013,155 | 12/1961 | Schiring | 250/439 R |
| 3,933,251 | 1/1976 | Schmedemann | 250/439 |

Primary Examiner—Craig E. Church
Assistant Examiner—Thomas P. O'Hare
Attorney, Agent, or Firm—Watts, Hoffmann, Fisher & Heinke

[57] ABSTRACT

An X-ray table of the tiltable type in which a tower assembly is movably carried by a table body. The tower assembly includes a mast or column that is carried by a carriage and movable relative to the carriage in a path transverse to the longitudinal extent of the table. The carriage is longitudinally movable relative to the table body. The carriage support is provided by cylindrical ways and bearing clusters each including four circumferentially spaced bearings that are arranged in diametrically opposed pairs. One bearing of each pair is eccentrically mounted for preload adjustment. The bearings of one pair are positioned such that their axes are perpendicular to the plane of resultant forces imposed on the bearings and the ways when the table is in a vertical orientation.

25 Claims, 8 Drawing Figures

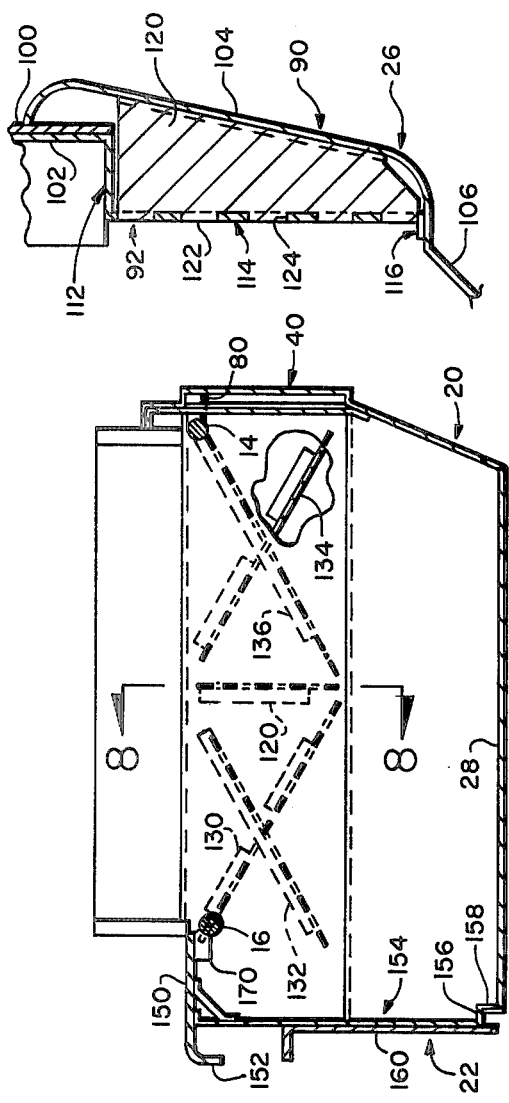
FIG. 7
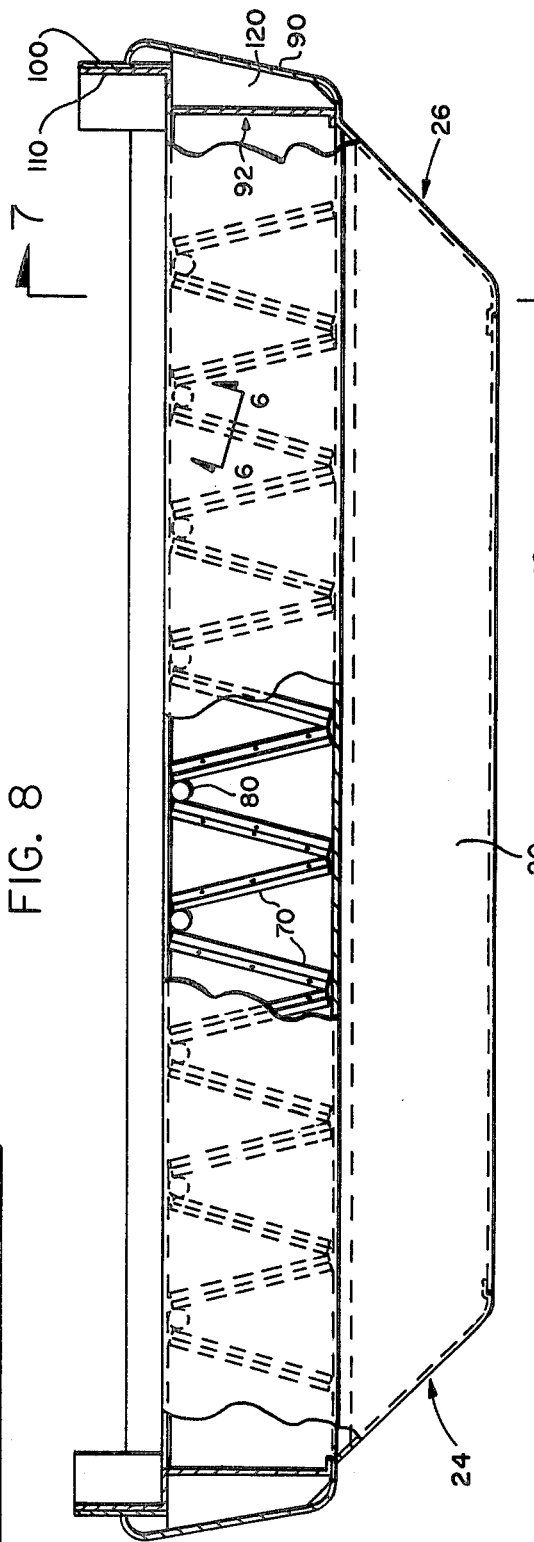
FIG. 8
FIG. 5
FIG. 6
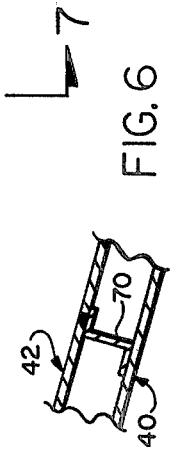

X-RAY TABLE

BACKGROUND OF THE INVENTION

1. Field of the Invention

The invention relates to X-ray tables and more particularly to tiltable tables

2. Description of the Prior Art

In so-called tilting type X-ray tables the table body is pivotally connected to a base or pedestal part so that it can be tilted in either direction from its normal position in which the patient-supporting surface is horizontal. This tilting permits a patient to be examined, in any angular table body position between two vertical positions. X-ray tables of this type are well known. Such a table typically includes a movable tower assembly which supports an X-ray tube within the body. The tower also supports radiation responsive devices, such as, a spot filmer, an image tube, and cameras for viewing the image tube output. These devices are usually above the patient supporting top of the table.

The tower assembly includes a column or tower within a forwardly extending portion that extends into the body of the table and underneath the top. This tower extension is mounted on carriage for movement horizontally in a direction transverse to the length of the table. The carriage is in turn supported on suitable ways in the body of the table for movement lengthwise of the table proper. The tower projects from the rear of the table body and supports a further carriage for movement towards and from the table proper. The further carriage carries the radiation detection device which is also movable throughout substantially the entire length of the table.

The movement of a tower assembly should be smooth and relatively effortless. It also should be linear to maintain accurate and consistent spatial relationship among a patient, the table's X-ray tube and the supported imaging devices. If the movement of the tower assembly and the table top is to be consistent and linear the table must be rigid and accurately manufactured.

Conventionally, tables have been constructed in which an upper frame and connected or integrally formed track elements supported the tower assembly. These track elements provided flat track surfaces which were in planes either parallel or perpendicular to the plane of the patient supporting surface.

The condition when smooth tower assembly movement is most difficult to achieve is when the table is tilted to θ vertical orientation. Since the tower carriage movement is vertical rather than horizontal, both the tower and counterweights of equal mass within the table must move vertically and easily. When the table is vertical the mass of the tower assembly, most of which is external of the table body, applies twisting forces to the tower assembly guide tracks and rollers. The resultant of these forces is a plane which is skewed with respect to the plane of the table top.

With prior tables, tower assembly rollers have been positioned such that some had their axes parallel to the table top while others had their axes perpendicular to the table top. Since the forces applied are skew with respect to the plane of the table top the forces applied to the rollers were not purely radial, but rather have significant axial vectors. This skewed force application caused the rollers to perform poorly and wear excessively.

Prior to the present invention various methods of constructions have been employed for supporting the column or tower in the table, but none are entirely satisfactory.

SUMMARY OF THE INVENTION

The present invention provides a novel and improved X-ray table, preferably of the tilting type pivotally supported on a base or pedestal, cantilevered thereon, if desired, for movement from one vertical position to the opposite vertical position and which employs cylindrical table ways for supporting the column or tower for movement lengthwise of the table body.

Rollers for support of the tower assembly are provided in clusters of 4. The rollers of each cluster are uniformly spaced, circumferentially speaking, to provide two pairs of diametrically opposed rollers. One roller of each pair is eccentrically mounted so that each roller pair can be independently adjusted to provide a precise and desired preloading of the rollers which are in the form of rolling element bearings.

The use of the cylindrical ways with the clusters of rollers provides a major advantage over the art. The advantage is, the rollers are positioned such that when the table is in a vertical orientation, the skewed resultant forces applied to the rollers by the weight of the tower are imposed radially on those rollers which bear the load. Expressed another way, the rollers are positioned such that their axes of rotation are neither parallel nor perpendicular to the plane of the table top but rather parallel or perpendicular to the plane of the resultant of forces applied to the rollers. This construction provides smooth, trouble-free bearing support for the tower in all table orientations and bearing life is extended.

The invention resides in certain constructions and combinations and arrangements of parts and further objects and advantages of the invention will be hereinafter referred to and others will be apparent from the following description of the preferred embodiment of the invention depicted in the accompanying drawings.

BRIEF DESCRIPTION OF THE DRAWINGS

FIG. 5 is a front elevational view of the body of the table, with parts broken away and parts in elevation;

FIG. 6 is a fragmentary sectional view approximately on the line 6—6 of FIG. 5;

FIG. 7 is a sectional view of the body of the table approximately on the line 7—7 of FIG. 5; and FIG. 8 is a sectional view approximately on the line 8—8 of FIG. 7.

DESCRIPTION OF THE PREFERRED EMBODIMENT

Figure 1:
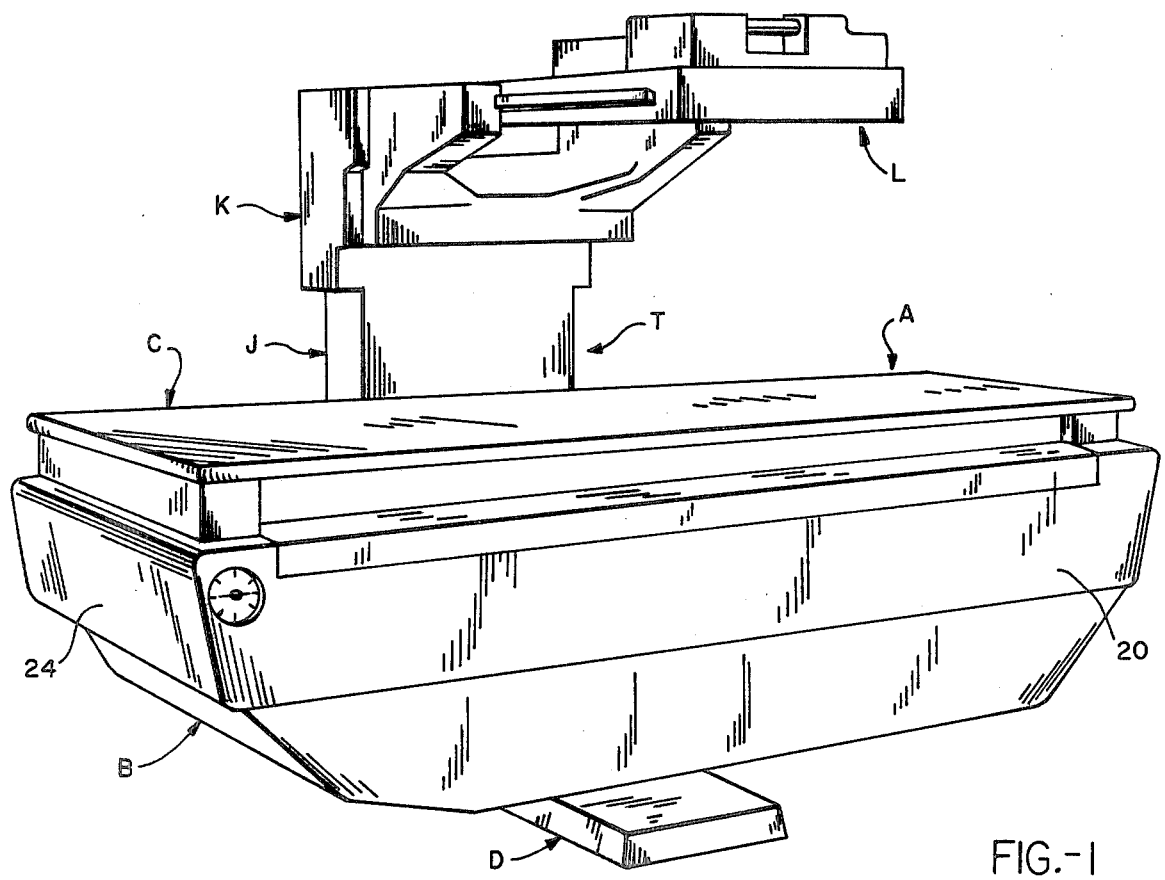
FIG. 1 is a perspective view of a 90—90 X-ray table assembly embodying the present invention.

Referring to the drawings FIG. 1 is a perspective view of an X-ray table of the 90—90 type embodying the present invention which is concerned primarily with the construction of the "tub" or body part of the table proper. The X-ray table is designated generally by the reference character T and comprises a table proper designated generally by the reference character A which includes a body B having a patient supporting top C. The table A is pivotally supported on a base part or pedestal D only a part of which is shown. The table A is cantilevered from the rear part of the pedestal D.

Figure 3:
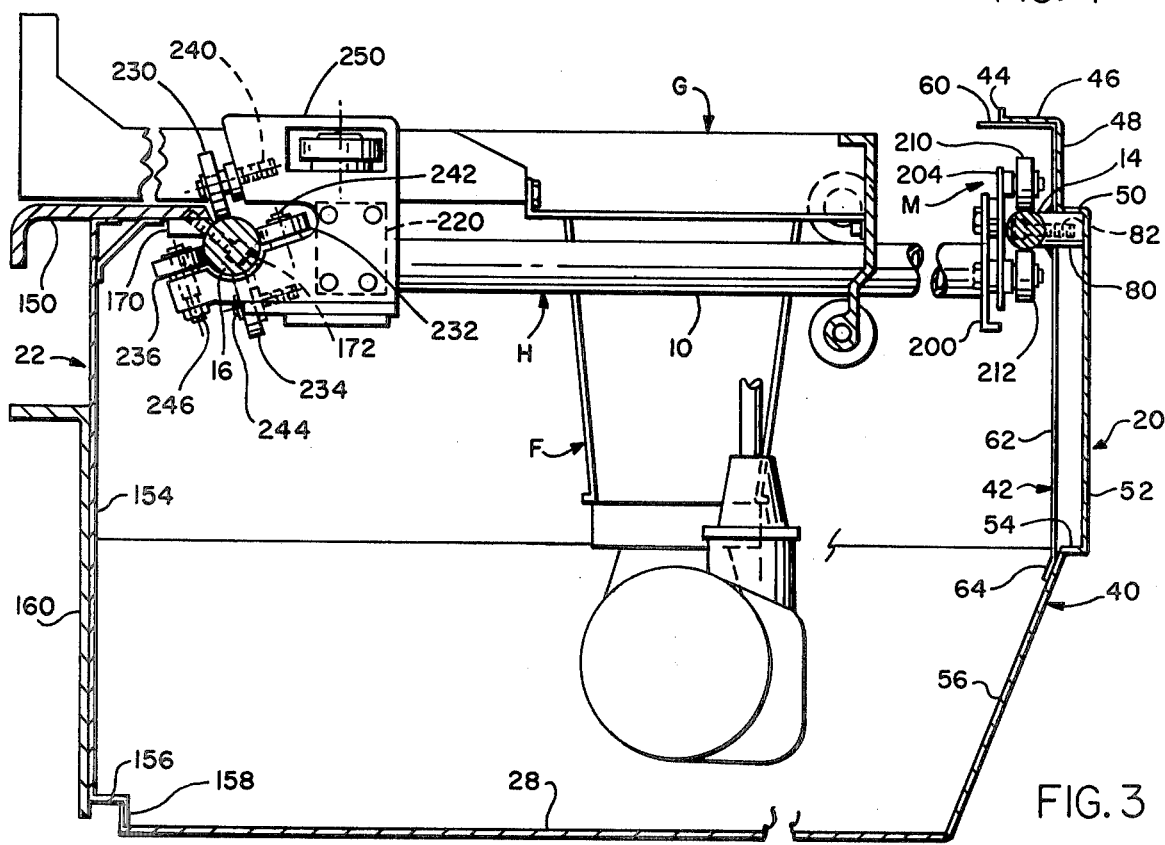
FIG. 3 is a fragmentary sectional view, with parts in elevation, approximately on the line 3—3 of FIG. 2 and looking towards the right, that is, in the direction of the foot of the table.
Figure 2:
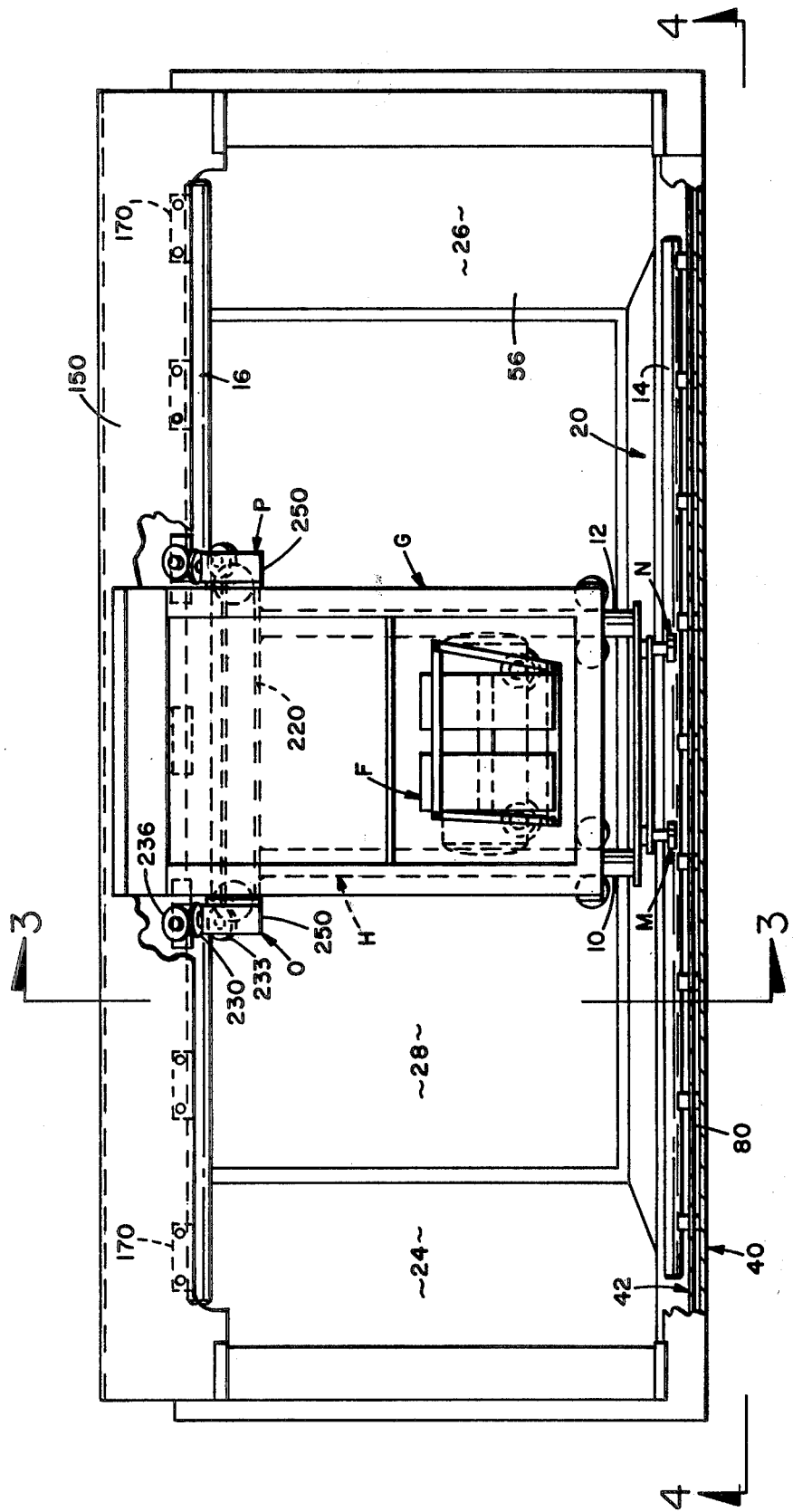
FIG. 2 is a fragmentary plan view of the body of the table with the patient supporting top removed and parts broken away.
Figure 4:
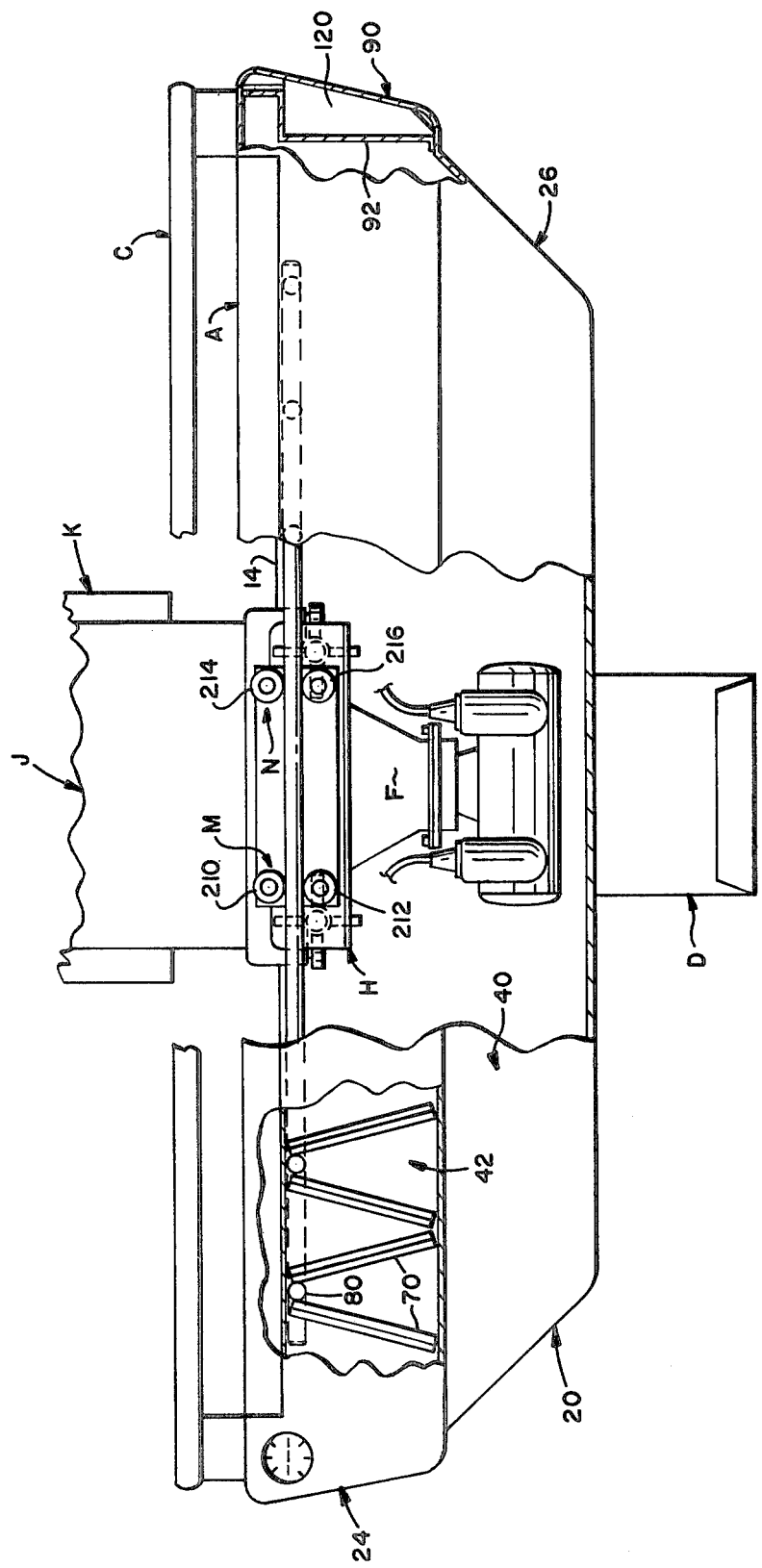
FIG. 4 is a sectional view, with parts broken away and parts in elevation, approximately on the line 4—4 of FIG. 2.

In the depicted table A the X-ray tube is in a holder F (FIG. 3) within the body of the table on a column or tower carriage G transversely movable of the table body on ways 10, 12 forming part of a carrier H movable longitudinally of the table body on ways 14, 16 in the table body. The tower carriage G extends rearwardly from the table body and carries, on its outwardly projection, a tower or column J which in turn supports a carriage K for vertical movement along the tower. The carriage K in turn supports a radiation detector carrier L movable transversely of the table proper A.

The particular construction of the X-ray table T, other than the way the column or tower carriage, or more particularily the carrier H, is supported in the table for movement lengthwise thereof forms no part of the present invention and may be of any commercial or known construction. The particular construction of the body of the table herein disclosed is the subject of a patent application of William H. Amor entitled "X-ray Table" and filed on even date herewith.

The four vertical front, rear, head end and foot end sides 20, 22, 24, 26 of the table B are constructed as sub-assemblies and then placed in a suitable fixture or jig and welded together. The bottom 28 (FIG. 3) is subsequently welded to the lower parts of the vertical sides of the table. After installation of the tower carriage ways 14, 16 and the other parts of the table located within the body B the table top C is installed.

The front side 20 of the table B comprises an outside sheet metal member 40 and an inside sheet metal member 42 commonly referred to as the front side, outside the inside skins, respectively. The outside member 40 forms the front outside of the table. The front outside skin has a short vertical flange 44 along its upper edge extending upwardly at right angle from a rather narrow horizontal panel 46 formed integral with a upper edge of rather narrow vertical panel 48. At the lower edge of panel 48 the member 40 bends horizontally to form a narrow horizontal panel 50 and then downwardly at right angles to the panel 50 to form a rather wide vertical panel 52 then inwardly at right angles to the panel 52 to form a second rather narrow horizontal panel 54 then downwardly and inwardly at a slight angle to form a lower inwardly inclined or sloping panel 56. The front inside skin 42 has a horizontal panel 60 abutting the underside of panel 46 and extending slightly inwardly of vertical panel 44. From panel 60 the member 42 bends downwardly at right angles to panel 60 to form a vertical panel 62. Panel 62 extends downwardly along the inside of the front outside member 40 to slightly beyond horizontal panel 54 and terminates in a relatively narrow panel 64 inclined inwardly at an angle the same as panel 56.

Prior to assembly of the members 40, 42 with one another rod-like reinforcing or stiffening members 70 (FIG. 6.) Z-shaped in cross-section are welded to the rear side of panel 52 of member 40. The members 70, of which there are eighteen in the depicted table, are slightly inclined to the vertical and arranged in a zig zag fashion with adjacent members inclined in opposite directions. Members 70 extend from panel 50 to panel 54 of member 40 with a space between the upper ends of each pair of members. After the members 40, 42 are assembled with one another the members 70 are spot welded to panel 62 of member 42. Thereafter cylindrical members 80 are inserted in suitable through apertures in members 42 between upper end of members 70 which ends are closest together. The members 80 of which there are nine in the depicted table form supports as will be hereinafter more specifically described for the tower carriage front way 16. The openings in member 42 through which the members 80 project are slightly larger than the members 80 so that members 80 can be aligned with one another as they are welded to member 42. Later the inner ends of members 80 have horizontally aligned duplicate V-grooves machined therein for the reception of the way 14 which is an accurately formed cylindrical bar. The way 14 is fixed to the members 80 by countersunk head screws 82 threaded in tapped apertures in members 80.

The head and foot ends 24, 26 of the table body B are generally similar in construction and merely the foot end 26 is described in detail. The foot end comprises outside and inside sheet metal members 90, 92 hereinafter sometimes referred to as the head end outside and inside skin, respectively. The upper edge of the outside skin member 90 is welded to a vertical member 100 having a narrow vertical panel 102 (FIG. 8) at its upper end. From the member 100 the member 90 curves downwardly and inwardly to a planar panel 104 which is inwardly inclined, at the lower end of panel 104 member 90 curves inwardly and then downwardly and inwardly to form a planar panel 106 which terminates at the bottom of the table B. The inner skin 92 has an upper vertical panel 110 which abuts member 102. At the lower end of panel 110 member 92 bends inwardly at right angle and forms horizontal panel 112 and then downwardly at right angles to form vertical panel 114 and terminates in a horizontal panel 116 welded to the lower end of panel 104 of member 90.

Before members 90 and 92 are assembled for welding one to the other, reinforcing members are welded to the inside of panel 104 of the outside skin member 26. One of these reinforcing members is a vertical plate 120 which extends from the panel 112 to the lower end of panel 114 of the inside skin member 92, and which is located intermediate the front and rear sides of the table. The edge of the plate 120 adjacent to the panel 104 is welded thereto and the opposite edge has a plurality of tabs 122 adapted to extend through apertures 124 in the inside skin member 92. Pairs of diagonal cross braces 130, 132 and 134, 136 (FIG. 7) are also welded to the inside of the panel 104 of the outside skin member 90. Like the inner edge of the reinforcing member 120, the inner edges, that is, the edges of the cross braces not adjacent to the outside skin member 90 are provided with tabs similar to the tabs 122 of the member 120, which tabs are inserted in suitable apertures or slots in the inside skin member 92. After the reinforcing members 120, 130, 132, 134, 136 are welded to the inside of the outside skin member 104, the skin members 90, 92 are assembled together with the tabs on the aforementioned reinforcing members extending through the previously-mentioned slots in the inside skin member 92 and the upper edge of the outside skin member 90 is welded to member 100 and the upper edge of the inside skin member 92 is also welded to the member 100 thus maintaining the inside and outside skin members together.

The rear side 22 of the body 20 of the table B comprises a longitudinally extending horizontal member 150 having a flange 152 along its rear edge which extends downwardly at right angles to the horizontal part of the member 150. A rear vertical panel member 154 having a narrow flange at its upper edge is welded to the underside of the member 150 and the lower end thereof terminates in a narrow, horizontal panel 156, the inner end of which terminates in a narrow vertical panel 158. A heavy reinforcing vertical member 160 extending longitudinally of the table is welded to the outside of the member 154.

With the vertical rear sides of the body 20 of the table B assembled as mentioned above, they are assembled in a jig or fixture with the outer corner thereof aligned in such a manner that no stress is incurred in the sheet metal parts thereof. During this assembly the inner skins of the end members 24, 26 are free to float relative to the outer skins thereof because the tabs of the reinforcing members 120, 130, 132, 134 are smaller than the apertures in the inner skin members through which they project. With the parts thus assembled, the reinforcing members in the end of the table are welded to the inner skins at opposite ends and the adjoining corners of the vertical sides are welded together. When the tub or body of the table is removed from the jig or fixture, the tub or body will not warp because no stress had been set up therein. The bottom member 28 is subsequently welded to the lower edges of the vertical side members.

As previously mentioned the tower carriage front way 14 is supported or carried by members 80 at the front of the table body 20. The rear tower carriage way 16 which is also an arcuately formed cylindrical bar is connected to the table B along the rear upper inside edge thereof by a plurality of bracket members 170 of which there are seven (7) in the depicted table. The members 170 are spaced along the rear side of the table and are bolted to the underside of the mbemer 150. The members have V grooves machined in their inner sides which are inclined downwardly and outwardly for the reception of the way 16 which is bolted to the bracket by machine screws 172.

The tower carriage H is supported on the ways 14, 16 by roller assemblies M, N, O, P located at the front head and foot corners of the tower carriage and at the head and foot sides of the carriage adjacent to the rear of the table B, respectively. The front ends of the tower carrier ways 10, 12 are welded to a vertical plate 200 having a forwardly extending horizontal flange along its lower edge. A longitudinally extending vertical plate 204 is connected to the plate 200 and spaced therefrom by suitable spacers. A top roller 210 rotatably supported on a stub shaft welded to the plate 204 engages and rides upon the top of way 14. A similar roller 212 rotatably supported by a stud shaft connected to the plate 204 by an adjustable eccentric bearing engages the lower side of the way 14. Upper and lower rollers 214, 216 similar to rollers 210, 212 and connected to plate 204 at the foot end of carriage H in like manners engage and travel along the top and bottom sides, respectively, of the way 14.

The rear ends of ways 10, 12 extend through a rectangular tubular member 220 extending lengthwise of the table B adjacent to the rear side of the table. The roller assemblies O, P for supporting the carriage H on the rear way 16 are alike except for differences incident to their being connected to opposite ends of the member 220 and merely assembly O adjacent to the head end of the table B will be described.

Roller assembly O comprises four rollers 230, 232, 234, 236 spaced ninety degrees (90°) apart about the way 16. The rollers are carried on stub shafts 240, 242, 244, 246, respectively, connected to a bracket 250 connected to the head end of member 220. Rollers 230, 234 lie in a plane which makes an angle of about thirty degrees (30°) with a vertical plane through the center of way 16 from which it will be evident rollers 230, 232 engage the upper surface of the way 16. Rollers 234, 236 engage the lower surface of the way 16. The rollers 230, 236 are eccentrically connected to the bracket 250 so that they can be adjusted relative to the way 16.

From the foregoing description of the preferred embodiment of the invention it will be apparent that an X-ray table body has been provided which incorporates cylinder ways upon which the carrier for the column or tower is supported by multiple rollers at the four corners of the carrier which securely support the carrier for free movement rotative to the table body without undue play or looseness.

While the preferred embodiment of the invention has been described in considerable detail, it will be apparent that the invention can be otherwise incorporated and it is the intention to hereby cover all adaptations, modifications and uses thereof which come within the scope of the appended claims.

I claim:

1. An X-ray table of the tiltable type wherein the table body is pivotally supported on a pedestal for tiltable movement through a range of positions from a position in which the plane of a patient supporting top is horizontal, said X-ray table comprising:
    (a) a table body having front and rear ways respectively adjacent to the top and to front and rear sides of the body;
    (b) a tower assembly including a carriage supported on said ways for movement lengthwise of said table body, the carriage being supported by roller assemblies adjacent to the front and rear sides of said table body and adjacent to the head and foot ends of said carriage;
    (c) each of said roller assemblies at the front side of said table body comprising two pairs of rollers, one pair of rollers engaging an upper portion of said front way and the other pair engaging a lower portion of said front way;
    (d) each front roller assembly including adjustment means for adjusting at least one of its rollers toward and away from a paired roller;
    (e) said roller assemblies adjacent to the rear side of said table body each comprising four rollers orientated substantially ninety degrees (90°) apart about the center of said rear way with two engaging an upper portion of said way at the rear side of said table body and two engaging a lower portion of said rear way, each of the rollers having an axis of rotation which is canted with respect to the plane of said top; and,
    (f) means for adjusting at least two of said rollers of each of said roller assemblies adjacent to the rear side of said table body towards and from said rear way.

2. The table of claim 1 wherein the axes of two of the rollers of each rear roller assembly are disposed generally perpendicular to a plane located by the resultant of forces applied to the rear way by the tower assembly when the patient supporting top is in a certain one of its positions.

3. The table of claim 2 wherein the certain position is that position at which the resultant of forces applied to the rear way is maximized.

4. The table of claim 2 wherein the certain position is a vertical position.

5. The table of claim 1 wherein the axes of two of the rollers of each rear roller assembly are disposed generally parallel to a plane located by the resultant of forces applied to the rear way by the tower assembly when the patient supporting top is in a certain one of its positions.

6. The table of claim 5 wherein the certain position is that position at which the resultant of forces applied to the rear way is maximized.

7. The table of claim 5 wherein the certain position is a vertical position.

8. An X-ray table assembly of the tiltable type wherein a table body assembly is pivotally supported on a pedestal for tiltable movement about a tilt axis through a range of positions from a position in which the plane of a patient supporting top is horizontal, said X-ray table including:
  (a) a tower assembly connected to the body assembly for movement longitudinally relative to the top;
  (b) one of the assemblies defining an elongated way for guiding the tower assembly during its longitudinal movement;
  (c) the other of the assemblies including at least one pair of rollers coacting with the way for guiding the tower during longitudinal movement; and,
  (d) said at least one pair of rollers comprising coacting rollers rotatable about substantially parallel axes each oriented other than parallel with the tilt axis generally perpendicular to a plane located by the resultant of forces applied by the tower assembly to the way when the patient supporting top is in a certain one of its positions.

9. The table of claim 8 wherein there are at least two roller subassemblies each including said at least one and another pair of rollers, the another pair of rollers having parallel axes of rotation each generally paralleling said plane.

10. The table of claim 8 wherein at least one roller of each pair is eccentrically mounted for adjustment toward and away from the other roller of the pair.

11. The table of claim 10 wherein the certain position is that position at which the resultant of forces applied to the rear way is maximized.

12. The table of claim 10 wherein the certain position is a vertical position.

13. An X-ray table of the tiltable type wherein the table body is pivotally supported for tiltable movement through a range of positions from a position in which the plane of a patient supporting top is horizontal, said X-ray table comprising:
  (a) a table body having front and rear ways respectively adjacent to the top and to front and rear sides of the body;
  (b) a tower assembly including a carriage supported on said ways for movement lengthwise of said table body, the carriage being supported by at least one roller assembly engaging the front way and at least one roller assembly engaging the rear way;
  (c) said one front way roller assembly comprising two pairs of rollers, one pair of rollers engaging an upper portion of the front way and the other pair of rollers engaging a bottom portion of the front way; and,
  (d) said one rear way roller assembly comprising four rollers oriented substantially ninety degrees (90°) apart about the center of said rer way with two of the four rollers engaging an upper portion and the other two rollers engaging a lower portion of said rear way, each of the four rollers having an axis of rotation which is canted with respect to the plane of said top.

14. The table of claim 13 wherein the axes of two of the rollers of each rear way roller assembly are disposed generally perpendicular to a plane located by the resultant of forces applied to the rear way by the tower assembly when the patient supporting top is in a certain one of its positions.

15. The table of claim 14 wherein the certain position is that position at which the resultant of forces applied to the rear way is miximized.

16. The table of claim 13 wherein the axes of two of the rollers of each rear roller assembly are disposed generally parallel to a plane located by the resultant of forces applied to the rear way by the tower assembly when the patient supporting top is in a certain one of its positions.

17. The table of claim 16 wherein the certain position is that position at which the resultant of forces applied to the rear way is maximized.

18. The table of claim 13 wherein the axes of two of the rollers of each rear way roller assembly are disposed generally perpendicular to a plane located by the resultant of forces applied to the rear way by the tower assembly when the patient supporting top is in a vertical position.

19. The table of calim 18 wherein the plane located by said resultant makes an angle of substantially thirty degrees (30°) with a vertical plane through the center of said rear way.

20. The table of claim 13 wherein the axes of two of the rollers of each rear roller assembly are disposed generally parallel to a plane located by the resultant of forces applied to the rear way by the tower assembly when the patient supporting top is in a vertical position.

21. The table of claim 20 wherein the plane located by said resultant makes an angle of substantially thirty degrees (30°) with a vertical plane through the center of said rear way.

22. An X-ray table of the tiltable type wherein the table body is pivotally supported for tiltable movement through a range of positions from a position in which the plane of a patient supporting top is horizontal, said X-ray table comprising:
  (a) a table body having front and rear ways respectively adjacent to the top and to front and rear sides of the body;
  (b) a tower assembly including a carriage supported on said ways for movement lengthwise of said table body, the carriage being supported by at least one roller assembly engaging the front way and at least one roller assembly engaging the rear way;
  (c) said one front way roller assembly comprising two pairs of rollers, one pair of rollers engaging an upper portion of the front way and the other pair of rollers engaging a bottom portion of the front way; and,
  (d) said one rear way roller assembly comprising four rollers oriented substantially ninety degrees (90°) apart about the center of said rear way with two of the four rollers engaging an upper portion and the other two rollers engaging a lower portion of said rear way, each of the four rollers having an axis of rotation which is canted with respect to the plane of the patient supporting top, wherein the axes of two of the four rollers are disposed generally perpendicular to a plane located by the resultant of forces applied to the rear way by the tower assembly when the patient supporting top is in a certain one of its positions, and the axes of the other two of said four rollers are disposed generally parallel to the plane located by said resultant.

23. The table of claim 22 wherein the certain position is that position at which the resultant of forces applied to the rear way is maximized.

24. An X-ray table fo the tiltable type wherein the table body is pivotally supported for tiltable movement through a range of positions from a position in which the plane of a patient supporting top is horizontal, said X-ray table comprising:
 (a) a table body having front and rear ways respectively adjacent to the top and to front and rear sides of the body;
 (b) a tower assembly including a carriage supported on said ways for movement lengthwise of said table body, the carriage being supported by at least one roller assembly engaging the front way and at least one roller assembly engaging the rear way;
 (c) said one front way roller assembly comprising two pairs of rollers, one pair of rollers engaging an upper portion of the front way and the other pair of rollers engaging a lower portion of the front way; and,
 (d) said one rear way roller assembly comprising four rollers oriented substantially ninety degrees (90°) apart about the center of said rear way with two of the four rollers engaging an upper portion and the other two rollers engaging a lower portion of said rear way, each of the four rollers having an axis of rotation which is canted with respect to the plane of the patient supporting top, wherein the axes of two of the four rollers are disposed generally perpendicular to a plane located by the resultant of forces applied to the rear way by the tower assembly when the patient supporting top is in a vertical position, and the axes of the other two of said four rollers are disposed generally parallel to the plane located by said resultant.

25. The table of claim 24 wherein the plane located by said resultant makes an angle of substantially thirty degrees (30°) with a vertical plane through the center of said rear way.

* * * * *